(12) United States Patent
Bullock et al.

(10) Patent No.: US 8,404,752 B2
(45) Date of Patent: Mar. 26, 2013

(54) METHOD OF TREATING TRAUMATIC BRAIN INJURY

(75) Inventors: M. Ross Bullock, Miami, FL (US); Bruce Spiess, Manakin-Sabot, VA (US); Deborah P. Thompson, Durham, NC (US)

(73) Assignees: Oxygen Biotherapeutics, Inc., Costa Mesa, CA (US); Virginia Commonwealth University, Richmond, VA (US)

( * ) Notice: Subject to any disclaimer, the term of this patent is extended or adjusted under 35 U.S.C. 154(b) by 768 days.

(21) Appl. No.: 12/460,409

(22) Filed: Jul. 17, 2009

(65) Prior Publication Data

US 2010/0178347 A1 Jul. 15, 2010

Related U.S. Application Data

(60) Provisional application No. 61/135,354, filed on Jul. 18, 2008, provisional application No. 61/212,721, filed on Apr. 15, 2009.

(51) Int. Cl.
*A61K 31/02* (2006.01)
(52) U.S. Cl. ........................... 514/759; 514/747
(58) Field of Classification Search .................. 514/759, 514/747
See application file for complete search history.

(56) References Cited

U.S. PATENT DOCUMENTS

| | | | |
|---|---|---|---|
| 3,911,138 A | 10/1975 | Clark, Jr. | |
| 3,977,988 A | 8/1976 | Tokiwa et al. | |
| 3,996,141 A | 12/1976 | Updike | |
| 4,173,654 A | 11/1979 | Scherer | |
| 4,289,499 A | 9/1981 | Clark, Jr. et al. | |
| 4,411,872 A | 10/1983 | Bramson | |
| 4,453,028 A * | 6/1984 | Lagow | 570/130 |
| 4,686,024 A | 8/1987 | Scherer, Jr. et al. | |
| 4,895,876 A | 1/1990 | Schweighardt et al. | |
| RE33,451 E | 11/1990 | Clark, Jr. | |
| 5,045,296 A | 9/1991 | Pfeffer et al. | |
| 5,158,536 A | 10/1992 | Sekins et al. | |
| 5,295,953 A | 3/1994 | Richard et al. | |
| 5,300,528 A | 4/1994 | Graybill et al. | |
| 5,399,334 A | 3/1995 | Kawakami et al. | |
| 5,437,272 A | 8/1995 | Fuhrman | |
| 5,490,498 A | 2/1996 | Faithfull et al. | |
| 5,637,318 A | 6/1997 | Gross et al. | |
| 5,674,913 A | 10/1997 | Clark, Jr. | |
| 5,824,703 A | 10/1998 | Clark, Jr. | |
| 5,840,767 A | 11/1998 | Clark, Jr. | |
| 6,167,887 B1 | 1/2001 | Clark et al. | |
| 6,204,296 B1 | 3/2001 | Weers et al. | |
| 6,346,228 B1 | 2/2002 | Choudhary et al. | |
| 2001/0023262 A1 | 9/2001 | Raynolds et al. | |
| 2005/0281890 A1 | 12/2005 | San | |
| 2007/0026024 A1 | 2/2007 | Drees | |
| 2009/0169630 A1 | 7/2009 | Ward et al. | |
| 2009/0202617 A1 | 8/2009 | Ward et al. | |
| 2010/0267842 A1 | 10/2010 | Kiral et al. | |
| 2011/0086923 A1 | 4/2011 | Thompson et al. | |
| 2011/0229575 A1 | 9/2011 | Clauson et al. | |
| 2011/0230566 A1 | 9/2011 | Tamargo et al. | |

FOREIGN PATENT DOCUMENTS

| | | |
|---|---|---|
| EP | 0521492 | 1/1993 |
| EP | 2 005 948 A9 | 12/2008 |
| EP | 2005948 | 12/2008 |
| WO | WO/91/03267 | 3/1991 |
| WO | WO/92/19232 | 11/1992 |
| WO | WO/92/19300 | 11/1992 |
| WO | WO/95/31191 | 11/1995 |
| WO | WO/97/19678 | 6/1997 |
| WO | WO/99/26604 | 6/1999 |
| WO | WO/2005/097208 | 10/2005 |
| WO | WO/2007/105978 | 9/2007 |
| WO | WO/2007/134304 | 11/2007 |
| WO | WO/2009/102487 | 8/2009 |
| WO | WO/2010/033187 | 3/2010 |
| WO | WO/2010/077671 | 7/2010 |

OTHER PUBLICATIONS

Woitzik et al., Neurological Research, 2005, 27(5):509-515.*
Woitzik et al. CAS: 143:415989, 2005.*
Cernak (2005) "Animal Models of Head Trauma" NeuroRx, 2(3):410-422.
Jones et al. (2006) "The effects of preinjury clopidogrel use on older trauma patients with head injuries" The American Journal of Surgery, 192(6):743-745.
Narayan et al. (2002) "Clinical Trials in Head Injury" Journal of Neurotrauma, 19(5):503-557.
Ringleb et al. (2004) "Benefit of Clopidogrel Over Aspirin Is Amplified in patients With a History of Ischemic Events" Stroke (35):528-532.
Saatman et al. (2008) "Classification of Traumatic Brain Injury for Targeted Therapies" J. Neurotrauam 25(7):719-738.
Stein et al. (2009) "Erythrocyte-Bound Tissue Plasminogen Activator is Neuroprotective in Experimental Traumatic Brain Injury" Journal of Neurotrauma 26(9):1585-1592.
Wong et al. (2008) "The Effects of Clopidogrel on Elderly Traumatic Brain Injured Patients" The Journal of Trauma Injury, Infection, and Critical Care 65(6)1303-1308.
U.S. Appl. No. 13/250,682, filed Sep. 30, 2011, Gerald Klein.
PCT International Search Report issued Oct. 19, 1995 in connection with PCT International Application No. PCT/US1995/05993. PCT International Search Report issued Apr. 1, 1997 in connection with PCT International Application No. PCT/US1996/18801.
PCT International Search Report issued Aug. 27, 1999 in connection with PCT International Application No. PCT/US1998/24632.
PCT International Search Report issued Oct. 17, 2007 in connection with PCT International Application No. PCT/US2007/68910.

(Continued)

*Primary Examiner* — Rei-tsang Shiao
(74) *Attorney, Agent, or Firm* — Gary J. Gershik; Cooper & Dunham LLP

(57) ABSTRACT

This invention provides for methods of treating a subject suffering from central nervous system injury, including traumatic brain injury, comprising administering to the subject an amount of a perfluorocarbon. This invention also provides for use of a perfluorocarbon in the manufacture of a medicament for treating a subject suffering from central nervous system injury including traumatic brain injury. This invention further provides for a pharmaceutical composition comprising a perfluorocarbon for use in treating a subject suffering from central nervous system injury, including traumatic brain injury.

33 Claims, 4 Drawing Sheets

OTHER PUBLICATIONS

Written Opinion of the International Searching Authority issued Oct. 17, 2007 in connection with PCT International Application No. PCT/US2007/68910.

International Preliminary Report on Patentability issued Nov. 17, 2008 in connection with PCT International Application No. PCT/US2007/068910.

Written Opinion of the International Searching Authority issued Sep. 22, 2009 in connection with PCT International Application No. PCT/US2009/04165.

Written Opinion of the International Searching Authority issued Dec. 9, 2009 in connection with PCT International Application No. PCT/US2009/05715.

PCT International Search Report issued Feb. 12, 2010 in connection with PCT International Application No. PCT/US2009/06159.

Written Opinion of the International Searching Authority issued Feb. 12, 2010 in connection with PCT International Application No. PCT/US2009/06159.

Written Opinion of the International Searching Authority issued Nov. 8, 2010 in connection with PCT International Application No. PCT/US2010/31320.

PCT International Search Report issued Nov. 8, 2010 in connection with PCT International Application No. PCT/US2010/31320.

International Preliminary Report on Patentability issued May 31, 2011 in connection with PCT International Application No. PCT/US2009/006159.

International Preliminary Report on Patentability issued Oct. 18, 2011 in connection with PCT International Application No. PCT/US2010/031320.

Clark, Jr. et al. (1979) "A New Look at the Vapor Pressure Problem . . . " Int. Congr. Ser.—Excerpta: 486 (Proc. Int. Symp. Perfluorochem. Blood ubstitutes, 4th), 55-67.

Clark, Jr. et al. (1989) "Physiological Evaluation of Fluorocarbon Emulsions with Notes on F-Decalin and Pulmonary Inflation . . . " Mat. Res. Soc. Symp. Proc. 110:129-134.

Clark, Jr. et al. (1992) "Response of the Rabbit Lung as a Criterion of Safety for Fluorocarbon Breathing and . . . " Biomat., Art. Cells & Immob. Biotech. (2-4):1085-1099.

Hoffmann et al. (1992) "Arterial Blood Gases and Brian Oxygen Availability Following Infusion of Intratracheal . . . " Biomat., Art. Cells & Immob. Biotech. 20(2-4):1073-1083.

Leach et al. (1993) "Perfluorocarbon-associated gas exchange (partial liquid ventilation) in respiratory distress syndrome: A prospective . . . " Critical Care Medicine. 21(9)12.

Lin et al. (1990) "The Synthesis of Highly Fluorinated Alkycyclohexanes for Use as Oxygen Carriers and the 19F and 13C NMR . . . " Journal of Fluorine Chemistry. 50:345-358.

Moore et al. (1982) "Synthesis and Physical Properties of Perfluorocompounds Useful as Synthetic Blood Candidates." Oxygen Carrying Colloidal Blood Substitutes. 50-60.

Okamoto et al. (1984) "Fate of perfluorochemical impurities contained in both perfluorodecaline (FDC) and . . . "Chemical Abstracts. (100)(3).

Remy et al. (1999) "Red blood cell substitutes: fluorocarbon emulsions and haemoglobin solutions." British Medical Bulletin. 55(1):277-298, p. 293, para 1.

Schürch et al. (1976) "Direct determination of surface tension in the lung." Proc. Natl. Acad. Sci. USA, Physiological Sciences. 73(12):4698-4702.

Shaffer et al. (1994) "Perfluorochemical Liquid as a Respiratory Medium." Art. Cells, Blood Subs., and Immob. Biotech. 22(2):315-326.

Smith et al. (1997) "Partial liquid ventilation: A comparison using conventional and high-frequency techniques in an animal model of . . . " Crit. Care Med. 25(7):1179-1185.

Tütüncü et al. (1993) "Comparison of Ventilatory Support with intratracheal Perfluorocarbon Administration and Conventional Mechanical . . . " Am. Rev. Respir. Dis. (148):785-792.

Varushchenko et al. (1996) "Thermodynamics of vaporization of some cyclic perfluorocarbons." Fluid Phase Equilibria. 126:93-104.

U.S. Appl. No. 12/589,202, filed Oct. 19, 2009, Huvard et al.

U.S. Appl. No. 12/590,996, filed Nov. 17, 2009, Huvard et al.

U.S. Appl. No. 12/653,343, filed Dec. 10, 2009, Ward et al.

PCT International Search Report issued on Sep. 22, 2009 in connection with International Application No. PCT/US2009/04165.

De Lange, F., et al. (2008) "Perfluorocarbon Adm. During Cardiopulmonary Bypass in Rats: An Inflammatory Link to Adverse Outcome." Anesthesia and Analgesia (106)(1): 24-31.

Mar. 7, 2012 Extended Eur. Search Rpt issued by EPO in connection w/ Eur. Pat. App. No. 09798325.8, regional stage of PCT Int. App. No. PCTJUS2009/004165, filed Jul. 17, 2009.

Kwon Taek Hyun et al. "Effect of perfluorocarbons on brain oxygenation . . . " Journal of Neurosurgery, vol. 103, No. 4, Oct. 2005, pp. 724-730.

Daugherty Wilson P et al. "Perfluorocarbon emulsion improves cerebral oxygenation . . . " Neurosurgery, vol. 54, No. 5, May 2004, pp. 1223-1230.

Woitzik Johannes et al. "Early administration of a second-generation perffuorochemical . . . " Neurological Research, vol. 27, No. 5, Jul. 2005, pp. 509-515.

Yang Zhong-Jin et al. "The effect of isovolemic hemodilution with oxycyte . . . ", PLOS ONE, vol. 3, No. 4, 2008, p. E2010.

Jan B. Wade: "Artificial blood goes from science fiction to science fact", Mar. 19, 2008.

Zhou Zhengwen et al. "Perfluorocarbon emulsions improve cognitive . . . " Neurosurgery, vol. 63, No. 4, Oct. 2008, pp. 799-806.

Mar. 7, 2012 Extended European Search Report issued by the European Patent Office (EPO) in connection with European Patent Application No. 09798325.8, regional stage of PCT International Application No. PCT/US2009/004165, filed Jul. 17, 2009 (Exhibit 1).

Kown Taek Hyun et al. "Effect of perfluorocarbons on brain oxygenation and ischemic damage in an acute subdural hematoma model in rats." Journal of Neurosurgery, vol. 103, No. 4, Oct. 2005, pp. 724-730 (Exhibit 2).

Daugherty Wilson P et al. "Perfluorocarbon emulsion improves cerebral oxygenation and mitochondrial function after fluid percussion brain injury in rats." Neurosurgery, vol. 54, No. 5, May 2004, pp. 1223-1230 (Exhibit 3).

Woitzik Johannes et al. "Early administration of a second-generation perfluorochemical decreases ischemic brain damage in a model of permanent middle cerebral artery occlusion in the rat." Neurological Research, vol. 27, No. 5, Jul. 2005, pp. 509-515 (Exhibit 4).

Yang Zhong-Jin et al. "The effect of isovolemic hemodilution with oxycyte, a perfluorocarbon emulsion, on cerebral blood flow in rats.", PLOS ONE, vol. 3, No. 4, 2008, p. E2010 (Exhibit 5).

Jan B. Wade: "Artificial blood goes from science fiction to science fact", Mar. 19, 2008 (Exhibit 6).

Zhou Zhengwen et al. "Perfluorocarbon emulsions improve cognitive recovery after lateral fluid percussion brain injury rats." Neurosurgery, vol. 63, No. 4, Oct. 2008, pp. 799-806 (Exhibit 7).

* cited by examiner

FIGURE 2
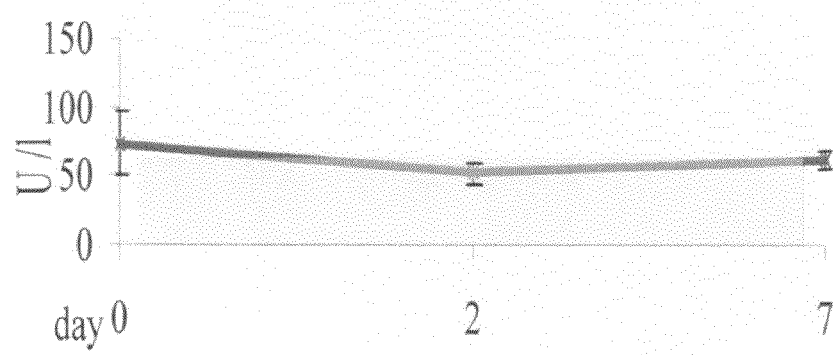
Fig. 2A
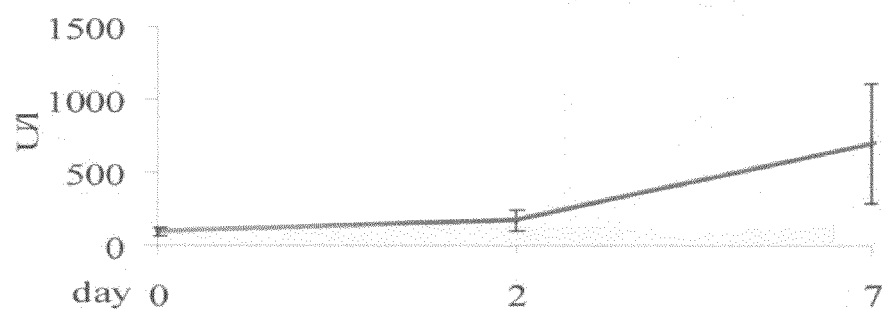
Fig. 2B
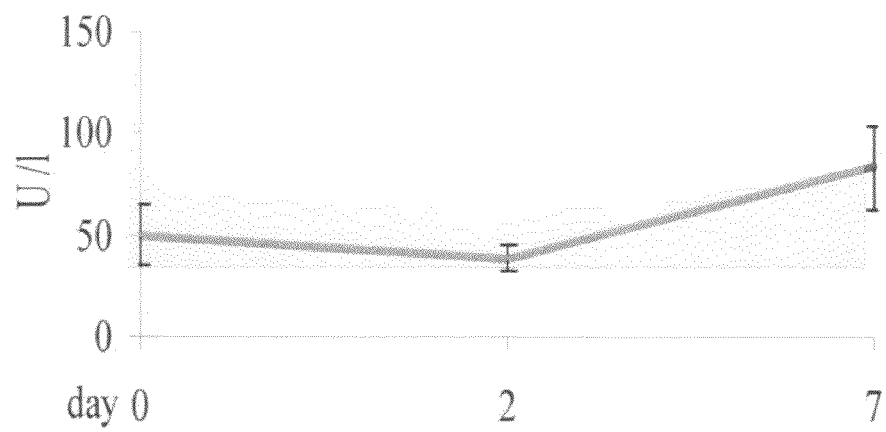
Fig. 2C

METHOD OF TREATING TRAUMATIC BRAIN INJURY

This application claims the benefit of U.S. Provisional Application No. 61/135,354, filed Jul. 18, 2008 and U.S. Provisional Application No. 61/212,721, filed Apr. 15, 2009, the entire content of which is hereby incorporated by reference herein.

The invention disclosed herein was made in part with government support under National Institute of Health Grant Nos. R01 N5047444 and R01 NS 055086. Accordingly, the U.S. Government has certain rights in this invention.

Throughout this application various publications are referenced. Full citations for these references may be found at the end of the specification immediately preceding the claims. The disclosures of these publications in their entireties are hereby incorporated by reference into this application to more fully describe the state of the art to which this invention pertains.

BACKGROUND OF THE INVENTION

Traumatic brain injury (TBI) may be caused by blunt injury (motor vehicle accident (MVA), falling or otherwise being struck in the head), penetrating injury (high velocity-bullet wound), or blast injury. Immediate neuronal, axonal and vascular destruction results from the impact of a blunt, bullet or blast injury. The amount of immediate tissue damage is highly variable depending upon the energy transfer at the point of impact and the medical status of the victim. In the civilian population, at least 200,000-300,000 significant blunt TBI events occur per year. Most of these are MVA, induced falls (particularly in the young and sports injuries), but bullet injuries may well add at least 25,000 more. Blast injury is the single largest killer of the "War on Terror". Casualties are approximately 4,000 dead and perhaps 300,000 have had one or more blast injury TBI events. In blast injury the military medical research community is just beginning to study the mechanisms and predictability of the injury. The effects of multiple sub-lethal blast injuries to the brain and or spinal cord are not known. It is known that after TBI and spinal cord injury there is an ongoing series of events that leads to tissue damage over the next 7-10 days. The initial injury sets up cellular events of calcium flux, ion leakage, cellular apoptosis, vascular insufficiency, neutrophil activation, clot formation, edema etc. All of these mechanisms further feed back into the neuronal apoptosis and cell death mechanisms perpetuating the cycle.

SUMMARY OF THE INVENTION

The subject application provides for a method of treating a human subject suffering from central nervous system injury comprising administering to the subject an amount of a perfluorocarbon effective to treat the human subject.

The subject application also provides for a method of treating a subject suffering from central nervous system injury comprising administering to the subject an amount of a perfluorocarbon effective to treat the subject, wherein the perfluorocarbon is perfluoro-tert-butylcyclohexane.

The subject application also provides for use of a perfluorocarbon in the manufacture of a medicament for treating a human subject suffering from central nervous system injury.

The subject application also provides for use of perfluoro-tert-butylcyclohexane in the manufacture of a medicament for treating a subject suffering from central nervous system injury.

The subject application also provides for a pharmaceutical composition comprising a perfluorocarbon for use in treating a human subject suffering from central nervous system injury.

The subject application also provides for a pharmaceutical composition comprising perfluoro-tert-butylcyclohexane for use in treating a subject suffering from central nervous system injury.

BRIEF DESCRIPTION OF THE FIGURES

FIGS. 2A-2C. (2A-2C) Shows that the liver enzymes in the tested patients in Example 1 remained stable, except for the ALT (2C) which increased from 39±6 U/L to 83±20 U/L over 5 days, and the alkaline phosphatase (2B) which increased from 185±30 U/L to 699±410 within 7 days. Globulin, albumin, total protein bilirubin (total, conjugated and unconjugated) remained in the normal range.

DETAILED DESCRIPTION OF THE INVENTION

Embodiments of the Invention

Figure 1:
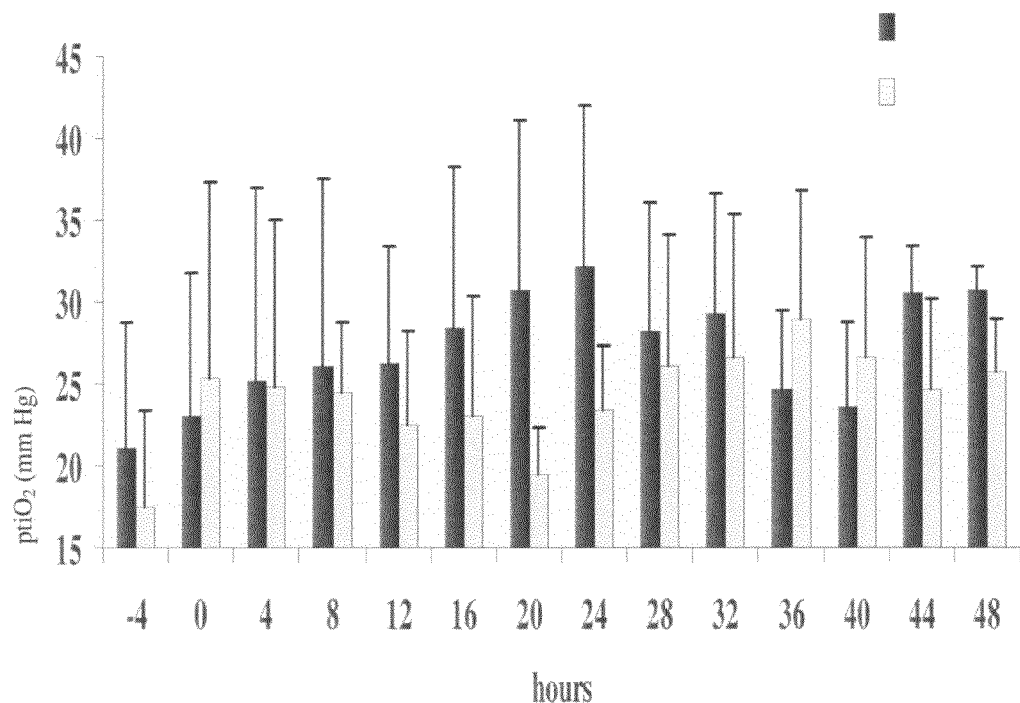
FIG. 1. Shows mean Tissue Oxygen Tension (ptiO$_2$) in traumatic brain injury patients #1-4 (dark gray bars) in Example 1 receiving a FiO$_2$ (fraction of inspired oxygen) of 0.5 and patients #5-8 (light gray bars) receiving a FiO$_2$ of 1.0 at 4 hrs before starting the Oxycyte® infusion (perfluoro-tert-butylcyclohexane). The FiO2 was maintained for 12 hours and then adjusted according to the blood gas analysis. A few minutes after beginning the Oxycyte® infusion, the ptiO$_2$ increased to 23±9 mmHg and 27±14 mmHg in the 1st and 2nd group respectively, reaching stable levels at 28±1.mmHg for 48 hours.
Figures 3, 3A, 3B, 3C, 3D:
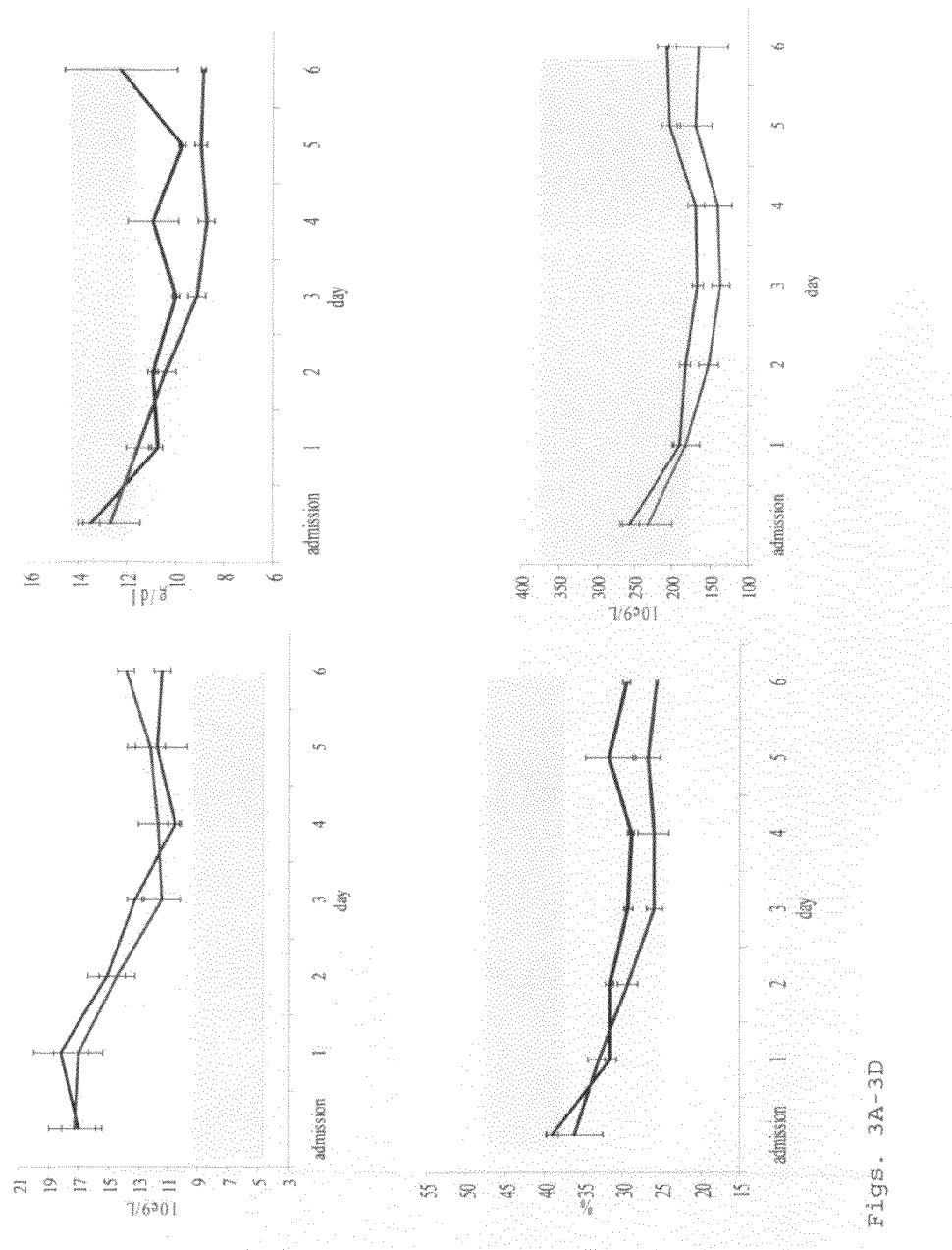
FIGS. 3A-3D. This figure shows effects of Oxycyte® (perfluoro-tert-butylcyclohexane) on white blood cell counts (3A), hemoglobin (3B), hematocrit (3C), and platelets (3D) in tested patients in Example 1. Normal value ranges are shaded gray, control group is the black line in each graph (n=36), Oxycyte® is the gray line in each graph (n=8).
Figure 4:
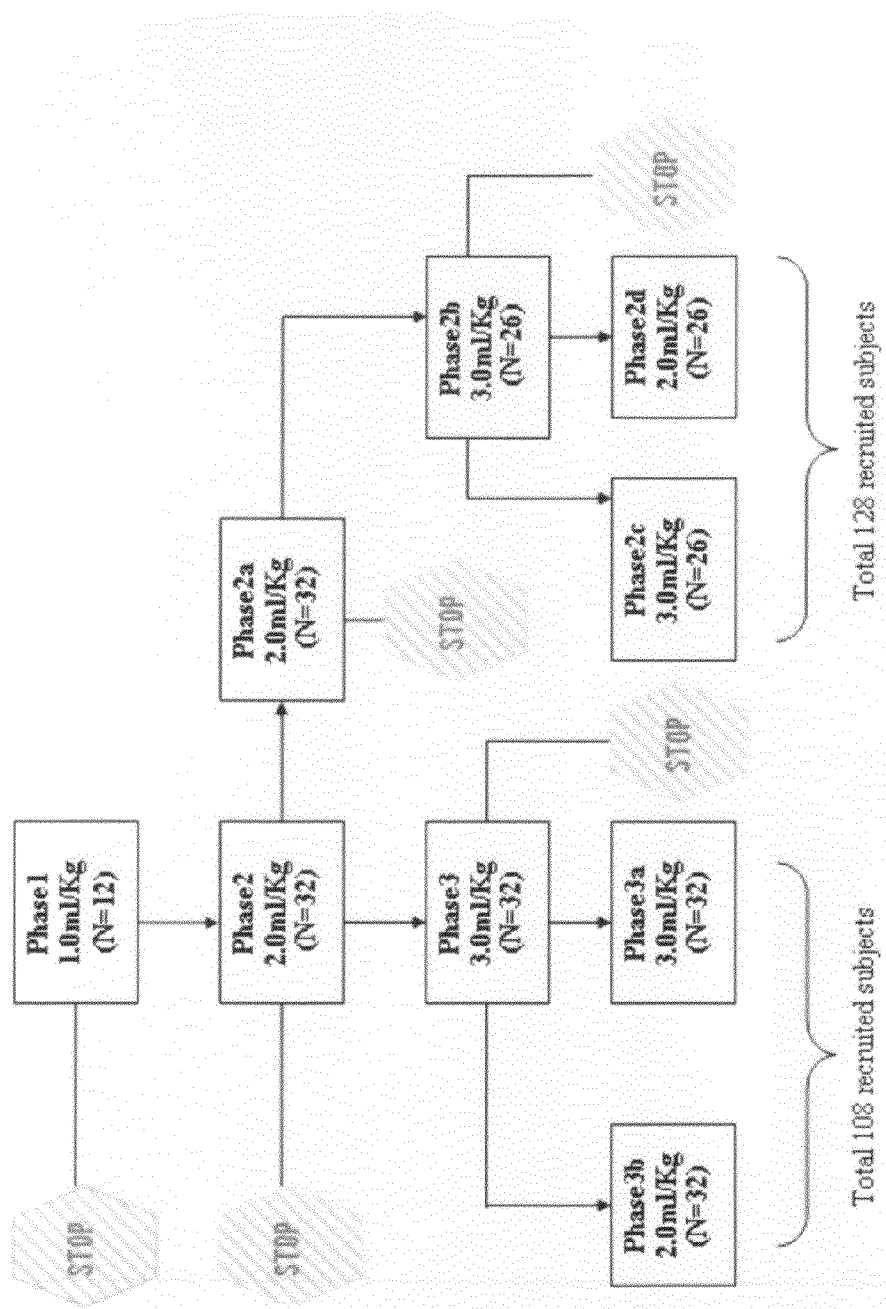
FIG. 4. Example 2 Dose Escalation Option Diagram.

The subject application provides for a method of treating a human subject suffering from central nervous system injury comprising administering to the subject an amount of a perfluorocarbon effective to treat the human subject.

In one embodiment, the perfluorocarbon is perfluoro-tert-butylcyclohexane.

The subject application also provides for a method of treating a subject suffering from central nervous system injury comprising administering to the subject an amount of a perfluorocarbon effective to treat the subject, wherein the perfluorocarbon is perfluoro-tert-butylcyclohexane.

In one embodiment, the central nervous system injury is brain injury. In another embodiment, the central nervous system injury is spinal injury. In another embodiment, the central nervous system injury is traumatic brain injury. In yet another embodiment, the traumatic brain injury is severe, non-penetrating traumatic brain injury.

In one embodiment, the subject had a score on the Glasgow Coma Scale of 3-9 prior to the administration of the perfluorocarbon. In another embodiment, the subject had a score on the Glasgow Coma Scale of 3-8 prior to the administration of the perfluorocarbon. In another embodiment, the subject had a score on the Glasgow Coma Scale of 4-9 prior to the administration of the perfluorocarbon In one embodiment, after the administration of the perfluorocarbon, the subject's functional outcome is improved, the subject's probability of survival is increased, the oxygen tension in a neuronal tissue of the central nervous system of the subject is increased, the progression of damage to, or ischemic damage to, or secondary ischemic damage to the central nervous system of the subject is reduced, and/or the loss of neuronal tissue in the central nervous system of the subject is reduced.

In one embodiment, the ischemic damage is ischemic brain damage. In another embodiment, the ischemic damage is ischemic spinal damage. In one embodiment, the neuronal tissue is cerebral tissue. In another embodiment, the neuronal tissue is spinal tissue.

In one embodiment, the functional outcome in the subject is assessed by the Glasgow Coma Scale score or Glasgow Outcome Scale-Extended score.

In one embodiment, the oxygen tension is increased from below 25 mmHg to 27 mmHg or above. In another embodiment, the oxygen tension is increased by 10-50% relative to a subject not administered the perfluorocarbon. In another embodiment, the oxygen tension is increased by 25-50% relative to a subject not administered the perfluorocarbon. In another embodiment, the oxygen tension is increased by 35-50% relative to a subject not administered the perfluorocarbon. In another embodiment, the oxygen tension is increased by 45-50% relative to a subject not administered the perfluorocarbon.

In one embodiment, the oxygen tension is increased for 24 hours or more. In another embodiment, the oxygen tension is increased for 36 hours or more.

In one embodiment, the perfluorocarbon is administered to the subject within 12 hours of the central nervous system injury.

In one embodiment, the above-described methods further comprise administering to the subject oxygen by inhalation, wherein the fraction of inspired oxygen is 21%-100%. In another embodiment, the fraction of inspired oxygen is 50%. In another embodiment, the oxygen is hyperbaric. In another embodiment, the subject is administered oxygen for 2 hours before the administration of the perfluorocarbon. In yet another embodiment, the subject is administered oxygen for 24 hours after the administration of the perfluorocarbon.

In one embodiment, the perfluorocarbon is administered intrathecally. In another embodiment, the perfluorocarbon is administered intravenously.

In one embodiment, the temperature of the perfluorocarbon administered is 0.1° C. to 5.0° C. below the subject's body temperature.

In one embodiment, the perfluorocarbon is in a perfluorocarbon emulsion. In another embodiment, the perfluorocarbon emulsion has a particle size of 0.3 microns or less. In yet another embodiment, the perfluorocarbon emulsion has a particle size of 0.05-0.1 microns.

In one embodiment, the perfluorocarbon emulsion is an egg yolk phospholipid emulsion buffered in an isotonic medium.

In one embodiment, the perfluorocarbon emulsion carries 42.5 ml of oxygen or more and 195.5 ml of carbon dioxide or more per 100 ml of perfluorocarbon emulsion. In another embodiment, the perfluorocarbon emulsion caries 43 ml of oxygen and 196 ml of carbon dioxide per 100 ml of perfluorocarbon emulsion.

In one embodiment, 0.5-3.5 ml of perfluorocarbon emulsion per kilogram of subject's body weight is administered to the subject. In another embodiment, 1.0-3.0 ml of perfluorocarbon emulsion per kilogram of subject's body weight is administered to the subject. In yet another embodiment, 3.0 ml of perfluorocarbon emulsion per kilogram of subject's body weight is administered to the subject.

In one embodiment, the perfluorocarbon emulsion is administered to the subject at a rate of 10-20 ml/min. In another embodiment, the perfluorocarbon emulsion is administered to the subject at a rate of 15 ml/min.

In one embodiment, 0.3-2.1 g of perfluorocarbon per kilogram of subject's body weight is administered to the subject. In another embodiment, 0.6-1.8 g of perfluorocarbon per kilogram of subject's body weight is administered to the subject. In yet another embodiment, 1.8 g of perfluorocarbon per kilogram of subject's body weight is administered to the subject.

In one embodiment, the perfluorocarbon is administered to the subject at a rate of 6.0-12.0 g/min. In another embodiment, the perfluorocarbon is administered to the subject at a rate of 9.0 g/min.

In one embodiment, the administration of the perfluorocarbon does not increase free radical generation in a neuronal tissue of the subject. In another embodiment, the above described methods further comprise administering to the subject an anti-coagulant and/or anti-inflammatory.

In one embodiment, the subject is human.

The subject application also provides for use of a perfluorocarbon in the manufacture of a medicament for treating a human subject suffering from central nervous system injury.

The subject application also provides for use of perfluorotert-butylcyclohexane in the manufacture of a medicament for treating a subject suffering from central nervous system injury.

For these uses, other embodiments described herein are applicable.

The subject application also provides for a pharmaceutical composition comprising a perfluorocarbon for use in treating a human subject suffering from central nervous system injury.

The subject application also provides for a pharmaceutical composition comprising perfluoro-tert-butylcyclohexane for use in treating a subject suffering from central nervous system injury.

For these pharmaceutical compositions, other embodiments described herein are applicable.

All combinations of the various elements are within the scope of the invention.

Terms

As used herein, and unless stated otherwise, each of the following terms shall have the definition set forth below.

As used herein, "administering" an agent, for example a perfluorocarbon ("PFC"), may be performed using any of the various methods or delivery systems well known to those skilled in the art. The administering can be performed, for example, intravenously (including intra-arterially), or intrathecally.

"Adverse event" or "AE" means any untoward medical occurrence in a clinical trial subject administered a medicinal product and which does not have a casual relationship with the treatment. An adverse event can therefore be any unfavorable and unintended sign including an abnormal laboratory finding, symptom, or diseases temporally associated with the use of an investigational medicinal product, whether or not considered related to the investigational medicinal product. "SAE" means serious adverse event.

"Central Nervous System" or "CNS" shall mean the brain and spinal cord of a subject.

"Closed head" injury or "non-penetrating" injury is an injury within the brain where skull penetration has not occurred.

As used herein, the term "effective" as in an amount effective to achieve an end refers to the quantity of a component that is sufficient to yield a desired therapeutic response without undue adverse side effects (such as toxicity, irritation, or allergic response) commensurate with a reasonable benefit/risk ratio when used in the manner of this disclosure. For example, an amount effective to treat a patient suffering from CNS injury without causing undue adverse side effects. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

"Emulsion" shall mean a mixture of two immiscible liquids. Emulsions are colloids wherein both phases of the colloid (i.e., the dispersed phase and the continuous phase) are liquids and one liquid (the dispersed phase) is dispersed in the other liquid (the continuous phase). The dispersed phase liquid can be in the form of particles suspended in the continuous phase liquid. "Perfluorocarbon emulsion" is an inert fluoridated oil in emulsion form containing a perfluorocarbon and having respiratory gas solubility. Perfluorocarbon emulsions may be made using standard techniques known in the art with a perfluorocarbon of choice. In one embodiment of this invention, the emulsion is a perfluorocarbon emulsion and the dispersed phase is perfluoro-tert-butylcyclohexane.

"Fraction of Inspired Oxygen" or "$FiO_2$" is the amount of oxygen in the air delivered to a subject. The $FiO_2$ is expressed as a number from 0 (0%) to 1 (100%). The $FiO_2$ of normal room air is 0.21 (21%), i.e., 21% of the normal room air is oxygen.

"Functional outcome" measures the extent of a subject's recovery from a certain injury or disorder, e.g., from central nervous system injury, in particular, traumatic brain injury. Functional outcome from traumatic brain injuries is often measured by the Glasgow Coma Scale and Glasgow Outcome Scale-Extended described below.

"Glasgow Coma Scale" or "GCS" shall mean the neurological scale used in determining Best Eye Response, Best Verbal Response, Best Motor Response (see Teasdale G., Jennett B., LANCET (ii) 81-83, 1974.). It is a widely used scoring system for quantifying level of consciousness following traumatic brain injury. The total score is the sum of the scores in three categories:

| Glasgow Coma Scale | | |
|---|---|---|
| Eye Opening Response | Spontaneous--open with blinking at baseline | 4 points |
| | Opens to verbal command, speech, or shout | 3 points |
| | Opens to pain, not applied to face | 2 points |
| | None | 1 point |
| Verbal Response | Oriented | 5 points |
| | Confused conversation, but able to answer questions | 4 points |
| | Inappropriate responses, words discernible | 3 points |
| | Incomprehensible speech | 2 points |
| | None | 1 point |
| Motor Response | Obeys commands for movement | 6 points |
| | Purposeful movement to painful stimulus | 5 points |
| | Withdraws from pain | 4 points |
| | Abnormal (spastic) flexion, decorticate posture | 3 points |
| | Extensor (rigid) response, decerebrate posture | 2 points |
| | None | 1 point |

The Glasgow Coma Scale provides a score in the range of 3-15. The lowest possible GCS score of 3 represents deep coma or death, while the highest possible GCS score of 15 represents a fully awake person. Generally, brain injury is classified as: Severe, with GCS 8, also a generally accepted definition of a coma; Moderate, GCS 9-12; and Minor/Mild, GCS≧13. The GCS is discussed further in Jennett, B. (2005) "Development of Glasgow Coma and Outcome Scales" Nepal Journal of Neuroscience, 2:24-28. "Glasgow Outcome Scale-Extended" or "GOS-E" is the scale developed to address the limitations of the original Glasgow Coma Scale, including the use of broad categories that are insensitive to change and difficulties with reliability due to lack of a structured interview format. Studies have found the GOS-E to be more sensitive to change than the original GCS, particularly in the case or mild to moderate TBI. (Levin, 2001). The GOS-E extends the original 5 GCS categories to 8. The 8 categories are: Dead, Vegetative State, Lower Severe Disability, Upper Severe Disability, Lower Moderate Disability, Upper Moderate Disability, Lower Good Recovery, and Upper Good Recovery. A structured interview is provided to improve reliability of rating. The GOS-E is discussed further in Wilson, J T L, et al. (1998) "Structured Interviews for the Glasgow Outcome Scale: Guidelines for Their Use" J. Neurotrauma, 15(8):573-585.

"Ischemia" means the restriction in blood supply, generally due to factors in the blood vessels, with resultant damage or dysfunction of tissue. When occurring in the brain (in the case of cerebral ischemia), ischemia means that there is insufficient blood flow to the brain to meet metabolic demand. This leads to poor oxygen supply or cerebral hypoxia and thus to the death of brain tissue or cerebral infarction/ischemic stroke. Unless otherwise specified, ischemia as used herein refers to both "primary ischemia" and "secondary ischemia".

"Primary" and "secondary" are classifications for the injury processes that occur in brain injury. In TBI, primary injury occurs during the initial insult, and results from displacement of the physical structures of the brain. Secondary injury occurs gradually and may involve an array of cellular processes. Secondary injury, which is not caused by initial mechanical damage, can result from the primary injury or be independent of it.

Therefore, "primary ischemia" is the restriction in oxygen supply resulting directly from the initial injury to the brain while "secondary ischemia" is the restriction in oxygen supply resulting from the process initiated by the initial injury, e.g., from complications of the initial injury, and can involve tissues that were unharmed in the primary injury. The primary and secondary classification of TBI is discussed in detail by Silver, J., et al. (2005) "Neural Pathology" *Textbook Of Traumatic Brain Injury*. Washington, D.C.: American Psychiatric Association. Chap. 2, pp. 27-33.

"Probability of survival" means the likelihood of a subject to survive the injury. The probability of survival is inversely correlated to mortality rate of a population suffering from the same condition and receiving the same treatment.

"Oxycyte®" is a perfluorocarbon ("PFC") emulsion oxygen carrier. The active ingredient in Oxycyte®, perfluoro-tert-butylcyclohexane ($C_{10}F_{20}$, MW-500), also known as F-tert-butylcyclohexane, is a saturated alicyclic PFC. Perfluoro-tert-butylcyclohexane is a colorless, completely inert, non-water soluble, non-lipophilic molecule, which is twice as dense as water, and boils at 147° C.

Physical properties of perfluoro-tert-butylcyclohexane are as follows:
Molecular Formula $C_{10}F_{20}$
Molecular Weight (g/mol) 500.08
Physical State @ Room Temp. Liquid
Density (g/mL) 1.97
Boiling Point (° C.) 147
Vapor Pressure (mmHg) @ 25° C. 3.8

Vapor Pressure (mmHg) @ 37° C. 4.4
Kinematic Viscosity (cP) 5.378
Refractive Index @ 20° C. 1.3098
Calculated Dipole Moment (Debye) 0.287
Calculated Surface Tension (dyne/cm) 14.4

Perfluoro-tert-butylcyclohexane carries about 43 mL of oxygen per 100 ml of PFC, and 196 ml of $CO_2$ per 100 ml of PFC. To be physiologically compatible the PFC in Oxycyte® is emulsified with egg-yolk phospholipids.

As formulated and manufactured, Oxycyte® is a sterile, non-pyrogenic emulsion consisting of submicron particles (medium diameter 200-250 nanometers) of perfluoro-tert-butylcyclohexane in an aqueous medium that is isotonic and mildly buffered to a neutral pH range. The composition of the 60% w/v emulsion is shown in Table 1.

TABLE 1

Composition of Oxycyte ® 60% w/v

| Component | Mg/mL |
|---|---|
| Perfluoro-tert-butylcyclohexane | 600.0 |
| Sodium Phosphate monobasic Monohydrate | 0.52 |
| Sodium Phosphate Dibasic Heptahydrate | 3.55 |
| Glycerin | 12.7 |
| Calcium Disodium Edetate Dihydrate | 0.2 |
| Egg Yolk Phospholipid | 40.0 |
| Vitamin E (dl-alpha-tocopherol) | 0.05 |
| Water for Injection (WFI) | 638.7 |

In the body the PFC emulsion is capable of uploading and unloading oxygen and $CO_2$ more efficiently than blood, and this process is concentration-gradient mediated (Henry's Law). Because the median size of the PFC droplets is approximately 40-50 times smaller than an erythrocyte, Oxycyte® is able to oxygenate tissues with narrowed capillaries, as occurs in brain contusions. Oxycyte® remains in the circulation for 20 to 24 hours after a single 30 minute rapid infusion of 3 mL/kg. PFC's are eliminated from the blood when macrophages scavenge the lipid particles. This is quite similar to how Intralipid is transported from the blood stream. PFC's are deposited in the liver and spleen. The lipid emulsion is slowly broken down slowly liberating PFC to be carried back to the lungs on various proteins and lipids wherein they are breathed out as a colorless, odorless and tasteless vapor. In non-human primates, the half-life of PFC in the liver and spleen was found to be dose related: at a dose of 1.8 g/kg (3 mL/kg), the half-life is approximately 12 hours.

"Oxygen tension" or "tissue oxygen tension" is denoted by $PTiO_2$ or simply $TiO_2$. Tissue oxygen tension is the directly measured local partial pressure of oxygen in a specific tissue. Brain tissue oxygen tension can be measured by the LICOX® Brain Oxygen sensor, which is a FDA approved clinical monitoring technique, which is endorsed by the AANS Guidelines for TBI management.

"Traumatic Brain Injury" or "TBI" shall mean central nervous system injury, i.e. CNS neuronal, axonal, glial and/or vascular destruction, from an impact. Such impacts include blunt impacts, bullet injury or blast injury.

"Severe TBI" is defined as a brain injury resulting in a loss of consciousness of greater than 6 hours and a Glasgow Coma Scale of 3 to 8.

Perfluoro-tert-butylcyclohexane ($C_{10}F_{20}$) is available, for example, as Oxycyte® from Oxygen Biotherapeutics Inc., Costa Mesa, Calif. In an embodiment, the Perfluoro-tert-butylcyclohexane has the following structure:

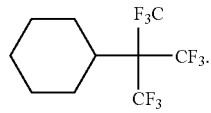

Injectable PFC emulsions can comprise excipients such as solubility-altering agents (e.g., ethanol, propylene glycol and sucrose) and polymers (e.g., polycaprolactones. and PLGA's) as well as pharmaceutically active compounds. The PFC emulsions may also comprise other pharmaceutically acceptable carriers suitable for intravenous or intrathecal administration.

The perfluorocarbon emulsions of the methods, uses and pharmaceutical compositions of the invention include perfluorocarbon-in-water emulsions comprising a continuous aqueous phase and a discontinuous perfluorocarbon phase. The emulsions typically include emulsifiers, buffers, osmotic agents, and electrolytes. The perfluorocarbons are present in the emulsion from about 5% to 130% w/v. Embodiments include at least about 40%, 45%, 50%, 55%, 60%, 65%, 70%, 75%, 80% and 85% w/v. A 60% w/v F-tert-butylcyclohexane emulsion may be used as the perfluorocarbon emulsion in one embodiment. Embodiments also include an egg yolk phospholipid emulsion buffered in an isotonic medium wherein the perfluorocarbon is present in the emulsion from about 5% to 130% w/v. Embodiments include at least about 40%, 45%, 50%, 55%, 60%, 65%, 70%, 75%, 80% and 85% w/v. A 60% w/v F-tert-butylcyclohexane emulsion may be used as the perfluorocarbon emulsion in one embodiment of an egg yolk phospholipid emulsion buffered in an isotonic medium.

The composition employed in the methods described herein may comprise a pharmaceutically acceptable additive.

It is understood that where a parameter range is provided, all integers within that range, and tenths thereof, are also provided by the invention. For example, "10-50%" includes 10.0%, 10.1%, 10.2%, 10.3%, 10.4% etc up to 50.0%.

All combinations and sub-combinations of the various elements of the methods described herein are envisaged and are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

Example 1

The key to intervention, and salvage of individual neurons and axons, is to provide adequate oxygen to the tissues at risk as rapidly as possible after injury. As the cycle of cell death, swelling, apopotosis, edema etc. continues successively more and more cells become injured and die. Thus, the sooner one can intervene with oxygen delivery to cells at risk, the quicker and greater numbers of cells are saved.

In the central nervous system (CNS), tissue cells die quickly when all oxygen is removed. Each cell that dies can translate into a circuit unable to be completed. CNS tissue cannot, at the present time, be regenerated by medical intervention. Early intervention to salvage the maximum number of cells represents a very real way to decrease the severity of injury and improve outcome for the patients.

Approximately ⅓ of severe head injury patients show reduced oxygen tension (<25 mmHg $ptiO_2$) during the first to 24 hours following injury, often due to reduced cerebral blood flow (CBF) caused by e.g. narrowed vessels, which can lead to post-traumatic brain damage and a significantly worse outcome (Zauner, 1997; Zauner, 1997). Thus, the prevention of secondary ischemia by the enhancement of early $O_2$ delivery should be of great benefit (Kwon, 2005).

Perfluorocarbons have the ability to dissolve large quantities of gases, including oxygen and carbon dioxide. Oxygen is physically dissolved in the perfluorocarbon emulsions and 90%-100% is released by simple diffusion in response to low tissue $pO_2$ according to Henry's Law. Perfluorocarbon (PFC) emulsions are inert fluoridated oils with enhanced respiratory gas solubility. PFC was created during the Manhattan Project for use as a liquid insulating agent with uranium 238. It was noted during that project that pure PFC, being not only inert and not reactive with any other compound, possessed a unique characteristic in that oxygen was profoundly more soluble than in water based media. From the 1960's to the present a number of PFC emulsions have been created, patented, and trialed in animal studies as well as human medicine. In 1990 Fluosol-DA-20%, a 10% v/v first generation PFC emulsion was approved by the United States Food and Drug Administration for the prevention of myocardial ischemia during balloon angioplasty.

The PFC Oxycyte® not only carries oxygen as a third compartment (erythrocytes and dissolved plasma being the other two) but it dramatically enhances oxygen delivery from red blood cells to tissues. Oxygen diffusion increases 50-fold in some studies thereby making the PFCs an oxygen supercharger. PFC emulsions are made up of pure PFC inside lipid membranes with a particle size far smaller than erythrocytes (0.05-0.1 microns). This small particle size allows PFC particles to flow to areas where erythrocytes perfusion is blocked by edema, clot and or inflammation. Because of the small particle size, coupled with enhanced oxygen diffusivity, oxygen can be delivered to tissues with very low, trickle, flow. PFC is known to increase cerebral blood flow and also to decrease inflammatory reactions. Also, PFC has enhanced gas carrying capacity for $CO_2$ as well as nitric oxide. These research observations may play roles in salvaging injured central nervous system cells.

In this study it is identified that oxygen can be delivered to tissues with only plasma (PFC contained) flow. The invention involves the use of PFC emulsion, and all other PFC-containing intravenous combination therapies (added other brain protection, inflammation reduction, or anticoagulant compounds) as a therapy for treatment and or prevention of central nervous system injury in TBI and spinal cord injury. The earliest intervention with infusion of PFC intravenously (IV) or intrathecally can improve/salvage the greatest amount of tissue. The PFC may be utilized in conjunction with or without added inhaled oxygen concentration. It may be utilized with hyperbaric oxygen delivery as well.

The specific use of the $3^{rd}$ generation PFC emulsion Oxycyte® is disclosed here, but the invention is not limited to this composition.

It should be noted that PFC emulsions deliver even more gas when cooled. Therefore, the utilization of cooling of the PFC emulsion prior to or during the act of infusion into the body may also be an adjunct and part of the invention disclosure as well.

Methods:

Nine severe closed head injury patients with an initial Glasgow Coma Scale (GCS) score of 3-9 were admitted to the study. Monitoring included cerebral perfusion pressure (CPP), Intracranial Pressure (ICP), and cerebral microdialysis, $ptiO_2$ measurements, CPP-directed blood pressure management, and arterial blood gases. Daily sampling for hematology, blood chemistry and coagulation parameters during days 1-4 after admission, and liver enzymes were measured. The first group of 4 patients were administered a $FiO_2$ of 0.5 starting 4 hours before giving the Oxycyte® infusion (lasting≈25 min) and maintained for a total of 12 hours, then adjusted according to the blood gas values, while the second group of 4 patients received a $FiO_2$ of 1.0 (See FIG. 1). The safety data were compared to a matched control group of 36 traumatic brain injury (TBI) patients (in one patient, the LICOX® ptiO2 monitor failed).

Results:

Immediately after beginning the Oxycyte® infusion, the $ptiO_2$ increased to 23±9 mmHg and 27±14 mmHg in the first and second group respectively, reaching stable levels at 28±1 mmHg and 28±1 mmHg respectively for 48 hours. The drop in hemoglobin, hematocrit and platelets was more pronounced in the Oxycyte® group, but the difference was not significant (see FIG. 3A-3D). The liver enzymes remained stable, except for the ALT which increased from 39±16 U/L to 83±20 U/L over 5 days, and the alkaline phosphatase which increased from 185±30 U/L to 699±410 within 7 days (see FIGS. 2A-2C) (difference not significant). Two Oxycyte® treated patients died, but the remainder (77%) were classified as good recovery or minimal disability at six months.

Conclusion:

The use of Oxycyte® in patients with severe TBI increased brain oxygenation. Severe adverse events and adverse events were not more frequent than in the controls.

Oxycyte® combined with either 50% or 100% $O_2$ can increase cerebral oxygenation after TBI. Outcome was better, in this small study, than expected. Moreover, no important changes in MAP, CPP and ICP after the infusion of Oxycyte® were seen, and there were no significant differences between the 2 groups in liver parameters, or platelets, and hemoglobin, although in both groups, values outside the normal range were seen. The incidence of Severe Adverse Events, and AE's were similar, in both groups.

Example 2

Clinical Trial—A randomized, Placebo Controlled, Double-Blind, Single Dose, Dose Escalation Study to Evaluate Oxycyte® in Patients with a Severe Non-Penetration Traumatic Brain Injury A randomized, placebo controlled, double-blinded, single dose, dose escalation Phase II clinical trial is conducted to assess the dose dependent safety, tolerability and efficacy of a single infusion of one of three ascending doses of Oxycyte® (1.0 mL/kg, 2.0 mL/kg, and 3.0 mL/kg) given within 12 hours of severe TBI combined with breathing 50% oxygen (or more, depending on standard of care for the patient's condition) for 2 hours before and 24 hours following infusion along with standard care.

Ischemic brain damage is found in 80% of patients who die from severe head injury and studies have shown that early, transient cerebral hypoperfusion of unknown origin is present in about 40% of these patients. (Adams, 1983; Bouma, 1992; Zauner, 1995; Zauner 1995; Zauner, 1997)

Recently, new techniques have permitted continuous monitoring of brain oxygen tension. (Adams, 1983; Bouma, 1992; Zauner, 1995) In a recently published study, it was documented that about one-third of severe head injured patients have reduced brain oxygen tension (<25 mm Hg $HgO_2$) for the first 6 to 12 hours following severe head injury. (Zauner 1995; Zauner, 1997; Doppenberg, 1997) In this group of patients with low brain oxygen, outcome is significantly worse. (Doppenberg, 1997; Robertson, 2004)

Reduced cerebral oxygenation may arise from four mechanisms: 1) reduced oxygen delivery by reduced cerebral blood flow; 2) reduced oxygen delivery by reduced hemoglobin content or hemoglobin function (e.g. carbon monoxide poisoning or anemia); 3) reduced oxygen uptake from the lungs (e.g. ARDS or severe lung disease); and 4) reduced oxygen unloading from the tissue (e.g. hypothermia). In severe head injury the cause for reduced cerebral oxygen tension in patients who do badly is unknown. (Doppenberg, 1997; Robertson, 2004)

Candidate mechanisms may include microvascular compromise due to astrocytic foot process swelling or reduced cerebral blood flow (CBF). Attempts to raise CBF by use of vasopressors and increasing cerebral perfusion pressure have not proven successful in a large National Institute of Health-funded trial conducted in Houston, Tex. (Verweij, 2000)

Recent studies have also convincingly shown that brain mitochondria are functionally abnormal after severe TBI. These mitochondria are transiently swollen and manifest reduced oxygen consumption, reduced ATP generation, and consequent buildup of brain lactate and reduction in extracellular fluid glucose due to a shift to anaerobic glycolysis. (Lifshitz, 2004; Chen, 2000; Tavalin, 1995) This, in turn, results in reduced ability of neurons to repolarize their membranes and thus, loss of function, and excess $K^+$ in the extracellular fluid, with consequent brain swelling and high intracranial pressure (ICP). (Reiner, 2000; Zhou, 2008)

In the laboratory, it was shown that augmenting tissue oxygen tension by use of hyperbaric oxygen (HBO), normobaric hyperoxia (100% $FiO_2$) and perfluorocarbons results in better functional outcome, brain oxygen consumption ($VO_2$) and less neuronal death after severe TBI in two rat models. (Tobias, 2004; Daugherty, 2004; Stiefel 2005; Nortje, 2008)

Recently, a Phase II study in patients with TBI was performed in which inspired oxygen content ($FiO_2$) was increased to 100% in a group of 51 severe TBI patients. (Stiefel 2005) In this group, brain oxygen tension uniformly increased and cerebral lactate in the extracellular fluid declined by 200%, suggesting that increased oxygen allowed lactate to be consumed in mitochondrial TCA cycle metabolism. (Tavalin, 1995) Moreover, intracranial pressure was significantly reduced and outcome was better. (Stiefel, 2005)

A recent study at Cambridge University in 13 patients with severe TBI showed that an $FiO_2$ of 50% significantly increased brain oxygen metabolic rate, as measured by positron emission tomography. (Nortje, 2006) In addition, the volume of ischemic brain tissue was significantly reduced. No pulmonary or other toxicity from 50% $FiO_2$ was seen. This study provides clear mechanistic evidence that increasing brain oxygen tension by even a small amount combined with $FiO_2$ of 50% can safely improve regional brain metabolism and reduce ischemic tissue damage by as much as 120 $cm^3$ in some patients.

Since increasing brain oxygen tension by both $FiO_2$ increase and HBO seem to be beneficial both in the lab and in patients, it was theorized that PFC enhanced oxygen delivery may provide the same benefit. Perfluorocarbon emulsions are especially attractive for increasing oxygenation of tissues for several reasons. First, they transport oxygen without the need for erythrocytes and hemoglobin can thus perfuse and oxygenate "peri-contusional" brain tissue in which it has been shown that capillaries are so narrowed as to impede RBC transport—a new possibility for therapy. Second, PFCs actually increase oxygen transport and oxygen tension in the tissues, which cannot be achieved with normobaric hyperoxia alone. PFCs increase the diffusional component of oxygen movement from erythrocytes to target tissues and have been shown to transport oxygen in asanguineous fluids with very low flows. Therefore, the enhanced oxygen delivery and mitochondrial preservation seen in prior animal models of TBI treated with PFC emulsions fit with these mechanistic explanations. The findings from the Phase II TBI trial both in improved outcome and oxygen levels in the brain are consistent with prior animal work as well as the mechanisms just outlined.

Dose Selection Rationale

The doses chosen for evaluation in this study are intended to establish the maximum safe dose and the minimum effective dose in the TBI population. That dose is expected to cause not more than an acceptable level of thrombocytopenia and deliver a meaningful improvement in brain oxygen tension levels.

In the phase I normal healthy volunteer (NHV) study in which doses ranging from 0.5 mL/kg (0.3 g/kg) to 3 mL/kg (1.8 g/kg) of Oxycyte® were administered, the lowest dose (0.5 mL/kg) was determined to be a "no effect" level (the equivalent of a No Observable Adverse Effect Level in preclinical studies) dose. Therefore, the lowest dose of Oxycyte® selected for evaluation in this study is the 1 mL/kg (0.6 g/kg) dose, which was found to be acceptably safe in the NHV study but also expected to have a sub-therapeutic dose effect on brain tissue oxygen tension; its primary purpose, however, is to demonstrate safety in a severe TBI population, particularly with regard to potential effect on platelets.

The choice of a 2 mL/kg (1.2 g/kg) dose was also determined to be acceptably safe in the NHV study; its effect on platelets and other safety parameters in the current TBI population is evaluated. If this dose produces thrombocytopenia in this population, it would be easily reversible with treatment. This dose is also aimed at demonstrating a "least effective dose" or effect upon brain tissue oxygen tension. The highest dose planned in this study (3.0 mL/kg; 1.8 g/kg) is less than one-fourth the highest dose tested in animal studies, was determined to be an acceptably safe dose in both the Phase I NHV study and 9-patient pilot TBI study, and is expected to have a therapeutic effect in patients with severe TBI. "Acceptably safe" at this dose level means that this dose may produce thrombocytopenia in this population, the severity of which is easily and rapidly reversible with treatment/transfusion and the risk of which is outweighed by the potential clinical benefits such as decreased mortality and better clinical outcomes. The primary purpose of this dose is to identify a dose that balances safety and therapeutic effect."

Indication

Severe, Non-Penetrating Traumatic Brain Injury

Sample Size (Number of Subjects and Study Sites)

128 patients are randomized to receive either a single dose of one of three dose levels of Oxycyte® or Normal Saline (NS) as the control. In the first dose level, patients are randomized 2:1 to receive either 1.0 mL/kg Oxycyte® (0.6 g/kg; n=8) or NS (n=4) for a total of 12 patients treated at this dose. At the next dose level, patients are randomized to receive either 2.0 mL/kg Oxycyte® (1.2 g/kg; n=30) or NS (n=12) followed either by a repeat of this dose cohort or advancement to the next highest dose level. At the highest dose level, patients are randomized to receive either 3.0 mL Oxycyte® (1.8 g/kg; n=20) or NS (n=6) followed either by a repeat of this dose cohort or a repeat of the previous dose cohort (2.0 mL/kg Oxycyte®) In the 3.0 mL/kg cohort, the number of patients who receive Normal Saline equal either 6 or 12, therefore, the total number of patients may equal either 26 or 32 in this group.

An evaluable patient is defined as a patient who has been treated with any amount of the study drug.

Between 68 and 88 patients are treated with one of three possible doses of Oxycyte® in this study; up to 40 patients in the control group receive Normal Saline (NS).

This study takes place at approximately eleven study sties: approximately 7 sites in Switzerland and approximately 4 sites in Israel.

Inclusion Criteria

Patients must meet all of the following criteria to be enrolled into the study:
1. Male or female 18-65 years of age inclusive at the time of study entry.
2. Severe, non-penetrating traumatic brain injury confirmed by head CT scan [Marshall Grade II-V or equivalent].
3. Glasgow Coma Scale 3-8 at screening and again just prior to administration of study drug.
4. Patients in whom brain tissue oxygen monitoring with a LICOX® probe/sensor is possible.
5. At least one reactive pupil at screening, confirmed again just prior to the administration of study drug.
6. Able to be dosed within 12 hours of injury (able to begin the infusion within 12 hours of injury).
7. Weigh 45 kg or more.
8. Either a) Family or legally authorized representative present who can give informed consent on behalf of the patient for study participation according to local law and regulations or b) an independent physician has determined that the patient is an appropriate candidate for study participation and the family or legally authorized representative has conveyed the "Presumable Will" of the patient to participate (which may be obtained retroactively where permitted by local regulations).

Exclusion Criteria

Patients meeting any one of the following criteria are excluded from the study:
1. Absence of a motor response.
2. Bilaterally fixed and dilated pupils.
3. Known allergy to any component of Oxycyte® or known severe allergy to egg.
4. History of severe TBI (previous to the current TBI) or any prior cerebral injury that required hospitalization and that may, in the Investigator's opinion, interfere with the results of the study.
5. Known history of HIV.
6. Known history of major liver disease (e.g., cirrhosis, necrosis or liver failure) or Chronic HBV or HCV infection.
7. Immersion injury.
8. Known or suspected brain tumor.
9. Known history of any of the following neurodegenerative diseases: Parkinson's disease, Huntington's disease, major stroke, seizure disorder, multiple sclerosis or cerebral aneurysm (unless clipped and stable, in which case patient may be included).
10. Platelet count of less than $10^9$/L ($100,000/mm^3$) at screening, prior to transfusion of any platelets and again just prior to dosing (during the stabilization period).
11. Core body temperature <34° C. or >38.5° C. at the time of screening and just prior to administration of study drug.
12. Coagulopathy (defined as INR>1.4 or prothrombin time >15 seconds or partial thromboplastin time >30 seconds).
13. Major liver, kidney, or cardiac injury requiring operative intervention.
14. Not expected to survive the next 24 hours.
15. Morbidly obese (BMI>40).
16. Concurrent use of Plavix® or an anti-coagulant other than 0.100 mg/day aspirin for any condition.
17. Total bilirubin >2×ULN.
18. Major pulmonary injury, including lung contusion, atelectasis, acute respiratory distress syndrome, or acute aspiration pneumonitis requiring >80% oxygen.
19. Known or suspected COPD, pulmonary edema, or congestive heart failure.
20. Any life threatening condition prior to the current injury or other disease or disorders that in the Investigator's opinion may put the patient at undue risk or confound the results of the study.
21. Patients with known congenital or acquired factor deficiencies (e.g., hemophilia, von Willebrand's disease), known qualitative platelet disorders (e.g., storage pool disease), known myeloproliferative disorders or bone marrow failure such as polycithemia vera, essential thermocythemia, myelodysplastic syndrome or any type of acute or chronic leukemia.
22. Penetrating head injury (e.g., gunshot).
23. Hemodynamically unstable just prior to administration of study drug (e.g., requires >6 L colloid or crystalloid fluid resuscitation).
24. Cardio-pulmonary resuscitation required following the current injury.
25. Women with a positive urine pregnancy test at screening.
26. Current participation in another clinical trial or participation in a clinical trial within 30 days prior to screening.
27. Patients serving in the military forces at the time of screening who do not have the required additional approval from the relevant authorities.

Treatment Plan

A randomized, placebo controlled, double-blinded, single dose, dose escalation Phase II clinical trial is conducted to assess the dose dependent safety, tolerability and efficacy of a single infusion of one of three ascending doses of Oxycyte® (1.0 mL/kg, 2.0 mL/kg, and 3.0 mL/kg) given within 12 hours of severe TBI combined with breathing 50% oxygen (or more, depending on standard of care for the patient's condition) for 2 hours before and 24 hours following infusion along with standard care.

At each dose level, patients receiving Oxycyte® is compared to a control group of patients who receive Normal Saline (NS). All patients receive 50% oxygen (or greater, if per standard care for a particular patient based on his/her condition) and standard of care.

The primary efficacy endpoint include the incidence in mortality, changes in brain tissue oxygen tension ($TiO_2$) and the Glasgow Coma Scale (GCS) before and after treatment with the study drug, and functional outcomes as measured by Glasgow Outcome Scale—Extended (GOS-E). Brain tissue oxygen tension is measured by the LICOX® Brain Oxygen Sensor, a FDA approved, clinically used monitoring technique that is endorsed by the American Association of Neurological Surgeons Guidelines for TBI management (Nortje, et al., 2008), to evaluate oxygen delivery to the brain.

Admission/Screening/Stabilization

After obtaining informed consent, the following assessments are performed to determine a patient's eligibility to participate in the study and to establish baseline measurements:
1. Glasgow Coma Scale.
2. Pupillary examination (pupil size, equality, shape and reactivity to light).
3. Medical History.
4. Demographics.

5. Concomitant medications (all medications taken within 12 hours of dosing are captured).
6. Urine drug screen (not exclusionary, capture only).
7. Blood alcohol level (record the level closest to dosing if multiple levels are available).
8. Occurrence of post-injury seizure.
9. Head CT scan (Marshall Grade/presence/absence of intracranial bleeding and hematoma).
10. Physical exam (including height and weight).
11. Assessment of extracranial and secondary injuries.
12. Approximate blood loss (due to injuries and any subsequent surgery combined).
13. Vital signs (blood pressure, heart rate, temperature).
14. Intracranial pressure (ICP) and cerebral perfusion pressure (CPP) (first reading available if probes were inserted prior to the stabilization period).
15. Peripheral oxygen saturation ($SpO_2$).
16. 12-lead ECG (rate, rhythm, abnormalities).
17. CBC with differential (hemoglobin, hematocrit, RBC, MCH, MCHC, WBC, basophils, eosinophils, monocytes, lymphocytes, vacuolated macrophages).
18. Platelet count, morphology and clumping (scale of 0-4).
19. Coagulation tests (PT, PTT, INR).
20. Chemistry (glucose, BUN, creatinine, sodium, potassium, chloride, calcium, bicarbonate, phosphorus, albumin, alkaline phosphatase, total bilirubin, LDH, GGT, ALT, and AST).
21. Urine pregnancy test for women of childbearing potential.
22. Urinalysis (color, appearance, specific gravity, pH, ketones, protein, nitrites, urobilinogen, bilirubin, glucose, occult blood and leukocyte esterase).
23. Date/time of injury.
24. Date/time of ICU admission (and later, discharge).

Patients who meet the above criteria undergo a 2-hour stabilization period prior to study drug administration. For all patients, $FiO_2$ is increased to 50% (or greater, if per standard care for a particular patient based on his/her condition) during this period and remain at 50% (or greater, per standard care) for 24 hours after completion of the infusion. During the stabilization period, patients are randomized and study drug prepared in order to allow product to come to room temperature after removal from refrigeration.

Before a patient is dosed, the following eligibility criteria are again confirmed:
Glasgow Coma Scale 4-9.
At least one reactive pupil.
Dosing begin within 12 hours of injury.
The following exclusion criteria are also re-confirmed:
Core body temperature <34° C. or >38.5° C.
Not expected to survive the next 24 hours.
Hemodynamically unstable; e.g., requires >6 L colloid or crystalloid fluid resuscitation.
Platelet count >10×9/L (100,000/$mm^3$).

Upon reconfirmation of eligibility criteria, the following baseline measurements are obtained just prior to dosing.
Vital Signs and $SpO_2$.
12-lead ECG.
ICP/CPP (first reading available after probes are inserted and a baseline reading just prior to dosing).
Sample collected for platelet function testing (PFA-100 or TEG (thromboelastography) when PFA-100 is not possible).
$TiO_2$ and brain temperature as measured by LICOX® probe/sensor.
Arterial blood gases (pH, $HCO_3$, $P_aO_2$, $P_aCO_2$, $S_aO_2$).
Coagulation tests.
CBC with differential.
Samples taken for D-dimers and fibrinogen.
Samples taken for amylase, cholesterol and triglycerides.
Cytokine samples (plasma) (pro-inflammatory cytokines IL-6, IL-8 and TNF-α) in a subset of patients (all patients in lowest dose cohort and 15 patients from each of the next highest dose cohorts) obtained for freezing and analysis by central lab.

Adverse event occurring during the stabilization period are recorded. All surgical procedures, transfusion and/or other treatments performed/administered prior to study drug administration are also recorded.

A patient who expires during the stabilization period is considered a screen failure; however, due to the fact that patients receive 50% oxygen during the stabilization period, which may be higher than they would normally receive (although some patients may require more than 50% oxygen per standard of care), relationship to study procedures are evaluated and clearly documented.

Drug Dosage and Route of Administration

Patients who continue to remain eligible for study participation receive a single infusion of study drug at the rate of 15 mL/minute and as specified in the dose escalation scheme described in the next section. Patients in the control group receive an infusion of NS at the same rate of 15 mL/minute. All patients receive standard care for severe traumatic brain injury as defined in the Guidelines for the Management of Severe Traumatic Brain Injury (AANS/Brain Trauma Foundation).

A single intravenous infusion of Normal Saline (NS) or one of three dose levels of the study drug—0.6 g/kg (1.0 mL/kg), 1.2 g/kg (2.0 mL/kg), and 1.8 g/kg (3.0 mL/kg) is started within 12 hours of injury and after a 2-hour stabilization period with 50% oxygen (or greater, if per standard care for a particular patient based on his/her condition).

During the infusion of the study drug, brain tissue oxygen tension and brain temperature, blood pressure, heart rate, body temperature, ICP, CPP, inspired oxygen $SpO_2$ and GCS are recorded every 5 minutes. For infusions lasting less than 5 minutes, these parameters are collected at the completion of the infusion. At 4 hours post-dosing, a blood sample is drawn for plasma storage for subsequent cytokine analysis.

The duration of infusion depends on the dose level and patient weight and thus the volume of study drug to be administered. Dose volumes range from 45 mL to approximately 300 mL. At an infusion rate of 15 mL/min, the duration of infusion ranges from 3-20 minutes.

50% Oxygen (or greater, depending on standard care for a particular patient's condition) is administered throughout the infusion and for 24 hours following the infusion. All other standard of care is administered according to standard TBI treatment guidelines.

Study Drug Administration and Dose Escalation

Three dose levels of Oxycyte® are administered during the study in a dose-escalation scheme as follows: 0.6 g/kg (1.0 mL/kg), 1.2 g/kg (2.0 mL/kg), and 1.8 g/kg (3.0 mL/kg). Each randomized patient who continues to meet all selection criteria after a 2-hour stabilization period that includes 50% (or greater) inspired oxygen receives a singled infusion of either one of the above Oxycyte® dose levels or Normal Saline (NS) (at a volume equal to the volume that would be administered if the patient were to receive Oxycyte®). Dose escalation depends on a complete review of all safety data and a monitoring committee (the DMC) and a formal determination to advance to the next highest dose; that determination may also include a formal risk-benefit analysis.

Phase 1: 1.0 mL/kg (0.6 g/kg) Oxycyte® (n=8) Versus Normal Saline (n=4)
  If one or more patients experience thrombocytopenia (defined as a platelet count <$10^9$/L) or any other serious adverse event within 7 days of study drug administration that is deemed possibly drug related, then escalation to the next phase does not proceed until a review by the DMC
Phase 2: 2.0 mL/kg (1.2 g/kg) Oxycyte® (n=20) Versus Normal Saline (n=12)
  At completion of this dose cohort (32 subjects who have completed the study through Day 7) data is analyzed and reviewed by the DMC in a formal review. Based on a review of the findings, the DMC decides among the following three courses of action:
  1. Stop the study due to safety concerns
  2. Remain at the 2.0 mL/kg Oxycyte® (Phase 2a)
  3. Increase the dose to 3.0 mL/kg Oxycyte® (Phase 3)
Phase 2a: 2.0 mL/kg (1.2 g/kg) Oxycyte® (n=20) Versus Normal Saline (n=12)
  This phase is only conducted if the DMC decides to remain at the Oxycyte® dose level administered in Phase 2. At the end of this phase (treatment of an additional 32 subjects who have then completed the study through Day 7), data is analyzed and reviewed by the DMC in a formal review. Based on a review of the findings, the DMC decides between the following two courses of action:
  1. Stop the study due to safety concerns
  2. Increase the dose to 3.0 mL/kg (1.8 g/kg) Oxycyte® (Phase 2b)
Phase 2b: 3.0 mL/kg (1.8/kg) Oxycyte® (n=20) Versus Normal Saline (n=6)
  At the end of this phase (26 subjects who have completed the study through Day 7), data is analyzed and reviewed by the DMC in a formal review. Based on a review of the findings, the DMC decides among one of the following three courses of action:
  1. Stop the study due to safety concerns
  2. Remain at 3.0 mL/kg Oxycyte® (Phase 2c)
  3. Reduce the dose to 2.0 mL/kg Oxycyte® (Phase 2d)
Phase 2c: 3.0 mL/kg (1.8 g/kg) Oxycyte® (n=20) Versus Normal Saline (n=6)
  This phase completes the study with the following sample sizes:
  3.0 mL/kg-40 patients (final selected dose)
  2.0 mL/kg-40 patients
  1.0 mL/kg-8 patients
  Control-40 patients
Phase 2d: 2.0 mL/kg Oxycyte® (n=20) Versus Normal Saline (n=6)
  This phase completes the study with the following sample sizes:
  3.0 mL/kg-20 patients
  2.0 mL/kg-60 patients (final selected dose)
  1.0 mL/kg-8 patients
  Control-40 patients
Phase 3: 3.0 mL/kg Oxycyte® (n=20) Versus 5% Normal Saline (n=12)
  After breaking the code, the DMC decides among the following three courses of action:
  1. Stop the study due to safety concerns
  2. Remain at 3.0 mL/kg Oxycyte® (Phase 3a)
  3. Reduce the dose to 2.0 mL/kg Oxycyte®(Phase 3b)
Phase 3a: 3.0 mL/kg Oxycyte® (n=20) Versus Normal Saline (n=12)
  This phase completes the study with the following sample sizes:
  3.0 mL/kg-40 patients (final selected dose)
  2.0 mL/kg-20 patients
  1.0 mL/kg-8 patients
  Control-40 patients
Phase 3b: 2.0 mL/kg Oxycyte® (n=20) Versus Normal Saline (n=6)
  This phase completes the study with the following sample sizes:
  3.0 mL/kg-20 patients
  2.0 mL/kg-40 patients (final selected dose)
  1.0 mL/kg-8 patients
  Control-40 patients
Safety Monitoring Plan
  An independent Data Monitoring Committee (DMC) reviews all safety data through Day 7 for all patients treated in the first dose cohort (n=12), after 32 patients have been treated in the second dose cohort, after 32 patients have been treated in the extended second dose cohort (if applicable), after 26 patients have been treated in the highest dose cohort and after 26 patients have been treated in the extended highest dose cohort (if applicable).
  Dose escalation stopping rules include an increased frequency and/or severity of serious, clinically significant or other adverse events of concern, including incidence and severity of thrombocytopenia, re-bleed, and nosocomial infection—as well as an increased frequency of unexpected mortality and/or transfusion—as compared to the control group. Prior to a final decision to discontinue dose escalation, a risk-benefit analysis is undertaken by the DMC.
Study Endpoints
  Efficacy: The incidence in mortality, brain tissue oxygen tension ($TiO_2$) levels, Glasgow Coma Scale (GCS) scores before and after treatment (through Day 30 or hospital discharge, whichever is first), and functional outcomes as measured by the Glasgow Outcome Scale-Extended (GOS-E, at Months 1, 3 and 6) is compared between treatment groups; $TiO_2$ is measured by LICOX® probe/sensor.
  The efficacy outcome variables are:
  1. Incidence in mortality;
  2. Changes in $TiO_2$;
  3. Change in severity of TBI;
  4. Changes in GCS; and
  5. Assessment of functional outcome as measured by GOS-E in patients with TBI.
  Brain tissue oxygen tension and brain temperature are measured for at least two hours prior to study drug administration (the stabilization period), every 5 minutes during the study drug infusion, and every hour for at least 48 hours following study drug administration. Thereafter, $TiO_2$ and brain temperature are collected daily, as long as monitoring continues per standard of care. Statistical comparisons are made between the control and Oxycyte® groups, at each does tier and across all tiers.
  Safety: Safety and tolerability is compared between treatment groups as measured by the incidence and severity of thrombocytopenia, frequency, severity and type of adverse events and serious adverse events, infectious processes, and re-bleed as confirmed clinically and by head CT scan, clinical laboratory tests (urinalysis, chemistry and hematology coagulation and platelet function tests), 12-lead ECG, intracranial pressure (ICP), cerebral perfusion pressure (CPP), vital signs (blood pressure, heart rate, peripheral oxygen saturation ($SpO_2$), arterial blood gases and requirement for platelet transfusion.

Primary Safety Outcome Variables are:
1. blood pressure;
2. heart rate;
3. body temperature;
4. intracranial pressure and cerebral perfusion pressure (ICP and CPP);
5. Hematology chemistry and urinalysis;
6. 12-lead ECG;
7. Transfusion requirements;
8. Coagulation parameters (PT, PTT, INR);
9. Platelet function tests;
10. Arterial blood gas analyses;
11. Incidence and severity of Adverse Events and Serious Adverse Events, including incidence of bleed or rebleed, which are collected and graded for severity according to "Common Terminology for Adverse Events", V3.0, 2006; and
12. Incidence of nosocomial infections, including but not limited to pneumonia/pulmonary events, wound infection, urinary tract infection and abscess formation.

Exploratory: Immune response to a single dose of Oxycyte® in a subset of TBI patients is evaluated. Pro-inflammatory cytokines (IL-6, IL-8 and TNF-α) are measured in a subset of patients (all patients from the lowest dose group and 15 patients from each of the next two highest dose groups) in order to evaluate the immune response to Oxycyte® in TBI patients.

$TiO_2$ is correlated with changes in severity of TBI and functional outcomes. Correlation of $TiO_2$ with GCS and functional outcomes are measured by GOS-E.

Results 1.0 mL/kg

A single infusion of 1.0 mL/kg of Oxycyte® in patients with severe, non-penetrating TBI (Glasgow Coma Scale of 3-8) in conjunction with 50% or more oxygen and other standard care improved oxygen delivery to the brain by increasing brain oxygen tension as measured by the LICOX® Brain Oxygen sensor in comparison to patients who received only Normal Saline as the control agent and 50% or more oxygen along with standard care. In addition, severe adverse events and adverse events were not more frequent than in the controls.

Moreover, a single infusion of 1.0 mL/kg of Oxycyte® in patients with severe, non-penetrating TBI (Glasgow Coma Scale of 3-8) in conjunction with 50% or more oxygen and other standard care reduced incidence of mortality, severity of the TBI as measured by GCS, and improved functional outcome as measured by GOS-E in comparison to patients who received only Normal Saline as the control agent and 50% or more oxygen along with standard care.

2.0 mL/kg

A single infusion of 2.0 mL/kg of Oxycyte® in patients with severe, non-penetrating TBI (Glasgow Coma Scale of 3-8) in conjunction with 50% or more oxygen and other standard care improved oxygen delivery to the brain by increasing brain oxygen tension as measured by the LICOX® Brain Oxygen sensor in comparison to patients who received only Normal Saline as the control agent and 50% or more oxygen along with standard care. In addition, severe adverse events and adverse events were not more frequent than in the controls.

Moreover, a single infusion of 2.0 mL/kg of Oxycyte® in patients with severe, non-penetrating TBI (Glasgow Coma Scale of 3-8) in conjunction with 50% or more oxygen and other standard care reduced incidence of mortality, severity of the TBI as measured by GCS, and improved functional outcome as measured by GOS-E in comparison to patients who received only Normal Saline as the control agent and 50% or more oxygen along with standard care.

3.0 mL/kg

A single infusion of 3.0 mL/kg of Oxycyte® in patients with severe, non-penetrating TBI (Glasgow Coma Scale of 3-8) in conjunction with 50% or more oxygen and other standard care improved oxygen delivery to the brain by increasing brain oxygen tension as measured by the LICOX® Brain Oxygen sensor in comparison to patients who received only Normal Saline as the control agent and 50% or more oxygen along with standard care. In addition, severe adverse events and adverse events were not more frequent than in the controls.

Moreover, a single infusion of 3.0 mL/kg of Oxycyte® in patients with severe, non-penetrating TBI (Glasgow Coma Scale of 3-8) in conjunction with 50% or more oxygen and other standard care reduced incidence of mortality, severity of the TBI as measured by GCS, and improved functional outcome as measured by GOS-E in comparison to patients who received only Normal Saline as the control agent and 50% or more oxygen along with standard care.

Example 3

A subject that has suffered a traumatic brain injury is administered a perfluorocarbon as soon as possible after the injury has occurred. Optionally, the subject is administered a perfluorocarbon emulsion, which can contain oxygen or be saturated with oxygen. Optionally, the subject is administered 50% or 100% oxygen by inhalation. The perfluorocarbon emulsion is Oxycyte® or a similar third-generation perfluorocarbon. The subject is found to have a reduced loss of neuronal tissue as compared to a comparable injured subject who does not receive the perfluorocarbon emulsion.

Example 4

A subject that has suffered a traumatic brain injury is administered a perfluorocarbon as soon as possible after the injury has occurred. Optionally, the subject is administered a perfluorocarbon emulsion, which can contain oxygen or be saturated with oxygen. Optionally, the subject is administered 50% or 100% oxygen by inhalation. The perfluorocarbon emulsion is Oxycyte® or a similar third-generation perfluorocarbon. The subject is found to have a reduced ischemic brain damage as compared to a comparable injured subject who does not receive the perfluorocarbon emulsion.

Example 5

A subject that has suffered a traumatic brain injury is administered a perfluorocarbon as soon as possible after the injury has occurred. Optionally, the subject is administered a perfluorocarbon emulsion, which can contain oxygen or be saturated with oxygen. Optionally, the subject is administered 50% or 100% oxygen by inhalation. The perfluorocarbon emulsion is Oxycyte® or a similar third-generation perfluorocarbon. The subject is found to have a reduced secondary ischemia as compared to a comparable injured subject who does not receive the perfluorocarbon emulsion.

Example 6

A subject that has suffered a traumatic brain injury is administered a perfluorocarbon as soon as possible after the injury has occurred. Optionally, the subject is administered a perfluorocarbon emulsion, which can contain oxygen or be saturated with oxygen. Optionally, the subject is administered 50% or 100% oxygen by inhalation. The perfluorocarbon emulsion is Oxycyte® or a similar third-generation perfluorocarbon. The subject is found to have an increased oxygen tension in a neuronal tissue (brain or spinal cord) as compared to a comparable injured subject who does not receive the perfluorocarbon emulsion.

REFERENCES

1. Adams J H, Graham D I, Gennerelli T A. Head Injury in Man and Experimental Animals: Neuropathology. Atca Neurochir. Suppl., 1983, 32:S15-S30.
2. Bouma G J, Muizelaar J P, Stringer W A, Choi S C, Fatouros P P, Young H F. Ultra-Early Evaluation of Regional Cerebral Blood Flow in Severely Head Injured Patients Using Xenon Enhanced Computerized Tomography. J. Neurosurg., 1992, 77:360-368.
3. Chen T, Qian Y, Di X, Rice A, Zhu J, Bullock R. Glucose/lactate dynamics after rat fluid percussion brain injury. J Neurotrauma 17(2)135-142, 2000.
4. Daugherty W P, Levasseur J E, Sun D, Spiess B D, Bullock M R. Perfluorocarbon Emulsion improves Cerebral Oxygenation and Mitochondrial Function after Fluid Percussion Brain Injury in Rats. Neurosurgery, 2004 May; 54(5): 1223-30; discussion 1230.
5. Doppenberg E M R, Watson J, Bullock R, Gerber M, Zauner A, Abraham D J. The Rationale for and Effects of Oxygen Delivery Enhancement to Ischemic Brain in a Feline Model of Human Stroke. An NY Acad. Sciences, 825:241-257.
6. Doppenberg, E, Watson, J., et al. Intraoperative monitoring of substrate delivery during aneurysm and hematoma surgery: initial experience in 16 patients. J. Neurosurg, 1997, 87:809-816.
7. Jennett, B. (2005) "Development of Glasgow Coma and Outcome Scales" Nepal Journal of Neuroscience, 2:24-28.
8. Kwon T H S D, Daugherty W P, Spiess B D, Bullock M R., Effect of perfluorocarbons on brain oxygenation and ischemic damage in an acute subdural hematoma model in rats. *J Neurosurg Oct*:724-730, 2005.
9. Levin, S. et al., (2001) "Validity and Sensitivity to Change of the Extended Glasgow Outcome Scale in Mild to Moderate Traumatic Brain Injury" *Journal of Neurotrauma.* June 2001, 18(6): 575-584.
10. Lifshitz J, Sullivan P G, Horda D, Weiloch T, McIntosh T. Mitochondrial damage and dysfunction in traumatic brain injury. Mitochondrion (5-6)705-713, 2004.
11. Menzel, M, Doppenberg E M, Zauner, A, Soukup J, Reinert M M, Bullock R. Increased Inspired Oxygen Concentration Improves Brain Tissue Oxygenation and Tissue Lactate Levels after Severe Human Head Injury. J. Neurosurg. 1999, 91(1):1-10.
12. Nortje et al.: Effect of hyperoxia on regional oxygenation and metabolism after severe traumatic brain injury: Preliminary findings. *Crit. Care Med* 36:273-281, 2008.
13. Nortje J, Gupta A K. The role of tissue oxygen monitoring in patients with acute brain injury. British Journal of Anesthesia, 2006, 97(1):95-106.
14. Reinert M, Khaldi A, Zauner A, Doppenberg E, Choi S, Bullock R. High levels of extracellular potassium and its correlates after severe head injury: Relationship to high ICP. J Neurosurg 93:810-817, 2000.
15. Robertson C. Personal communication, 2004.
16. Silver, J., et al. (2005) "Neural Pathology" *Textbook Of Traumatic Brain Injury. Washington, D.C.: American Psychiatric Association. Chap.* 2, pp. 27-33.
17. Stiefel M F, et al. Reduced mortality rate in patients with severe traumatic brain injury treated with brain tissue oxygen monitoring. J Neurosurg 2005 November; 103(5):805-811.
18. Tavalin S J, Ellis E F, Satin L S. Mechanical perturbation of cultured cortical neurons reveals stretch induced delayed depolarization. Neurophysiol. 74, 2767-2773, 1995.
19. Tobias C, Reinert M, Seiler R, Gilman C, Scharf A, Bullock R. Normobaric hyperoxia induced improvement in cerebral metabolism and reduction in intracranial pressure in patients with severe head injury: a prospective cohort matched study. J. Neurosurg. 101:435-444, 2004.
20. Valadka A. Gopinath S P, Contant C F, Uzura M, Robertson C S. Relationship of Brain Tissue PO2 to Outcome After Severe Head Injury. Crit. Care Med., 1998, 26:1576-1581.
21. Verweij B, Muizelaar P, Vinas F, Patterson P, Xiong Y, Lee C P. Impaired cerebral mitochondrial function after traumatic brain injury in humans. J Neurosurg 93(5):815-820; 2000.
22. Wilson, J T L, et al. (1998) "Structured Interviews for the Glasgow Outcome Scale: Guidelines for Their Use" J. Neurotrauma, 15(8):573-585.
23. Zauner A, Bullock R, Di X, Young HF. Brain Oxygen, CO2, pH, and Temperature Monitoring: Evaluation in the Feline Brain. Neurosurgery, 1995, 37:1167-1177.
24. Zauner A, Bullock R, Young HF. Continuous. Brain Oxygen, CO2, pH and Temperature Monitoring in Neurosurgical Patients. Neurosurgery, 1995, 37:570-575.
25. Zauner A, Doppenberg E, Woodward J J, Allen C, Jebraili S, Young H F, Bullock R: Multiparametric continuous monitoring of brain metabolism and substrate delivery in neurosurgical patients. *Neurol Res* 19:265-273, 1997.
26. Zauner A, Doppenberg E M, Woodward J J, Choi S C, Young H F, Bullock R: Continuous monitoring of cerebral substrate delivery and clearance: initial experience in 24 patients with severe acute brain injuries. *Neurosurgery* 41:1082-1091; discussion 1091-1083, 1997.
27. Zhou A, Sun D, Altemi N, Levasseur J, Hamm R, Daugherty W, Spiess B, Bullock R. Perfluorocarbon emulsion improves cognitive recovery following fluid percussion brain injury in rats. Neurosurgery. 63:799-807, 2008.

What is claimed is:

1. A method of treating a human subject suffering from traumatic central nervous system injury comprising administering to the human subject an amount of a perfluorocarbon effective to treat the subject, wherein the perfluorocarbon is perfluoro-tert-butylcyclohexane.

2. The method of claim 1, wherein the traumatic central nervous system injury is traumatic brain injury.

3. The method of claim 2, wherein the traumatic brain injury is severe, non-penetrating traumatic brain injury.

4. The method of claim 1, wherein the subject had a score on the Glasgow Coma Scale of 3-9 prior to the administration of the perfluorocarbon.

5. The method of claim 1, wherein after the administration of the perfluorocarbon, the subject's functional outcome is improved, the subject's probability of survival is increased, the oxygen tension in a neuronal tissue of the central nervous system of the subject is increased, the progression of damage to, or ischemic damage to, or secondary ischemic damage to the central nervous system of the subject is reduced, and/or the loss of neuronal tissue in the central nervous system of the subject is reduced.

6. The method of claim 5, wherein the functional outcome in the subject is assessed by the Glasgow Coma Scale score or Glasgow Outcome Scale-Extended score.

7. The method of claim 5, wherein oxygen tension is increased from below 25 mmHg to 27 mmHg or above.

8. The method of claim 5, wherein oxygen tension is increased by 10-50% relative to a subject not administered the perfluorocarbon.

9. The method of claim 5, wherein oxygen tension is increased for 24 hours or more.

10. The method of claim 1, wherein the perfluorocarbon is administered to the subject within 12 hours of the central nervous system injury.

11. The method of claim 1, further comprising administering to the subject oxygen by inhalation, wherein the fraction of inspired oxygen is 21%-100%.

12. The method of claim 11, wherein the fraction of inspired oxygen is 50%.

13. The method of claim 11, wherein the oxygen is hyperbaric.

14. The method of claim 11, wherein the subject is administered oxygen for 2 hours before the administration of the perfluorocarbon.

15. The method of claim 11, wherein the subject is administered oxygen for 24 hours after the administration of the perfluorocarbon.

16. The method of claim 1, wherein the perfluorocarbon is administered intrathecally.

17. The method of claim 1, wherein the perfluorocarbon is administered intravenously.

18. The method of claim 1, wherein the temperature of the perfluorocarbon administered is 0.1° C. to 5.0° C. below the subject's body temperature.

19. The method of claim 1, wherein the perfluorocarbon is in a perfluorocarbon emulsion.

20. The method of claim 19, wherein the perfluorocarbon emulsion has a particle size of 0.3 microns or less.

21. The method of claim 20, wherein the perfluorocarbon emulsion has a particle size of 0.05-0.1 microns.

22. The method of claim 19, wherein the perfluorocarbon emulsion is an egg yolk phospholipid emulsion buffered in an isotonic medium.

23. The method of claim 19, wherein the perfluorocarbon emulsion caries 43 ml of oxygen and 196 ml of carbon dioxide per 100 ml of perfluorocarbon emulsion.

24. The method of claim 19, wherein 0.5-3.5 ml of perfluorocarbon emulsion per kilogram of subject's body weight is administered to the subject.

25. The method of claim 24, wherein 1.0-3.0 ml of perfluorocarbon emulsion per kilogram of subject's body weight is administered to the subject.

26. The method of claim 19, wherein the perfluorocarbon emulsion is administered to the subject at a rate of 10-20 ml/min.

27. The method of claim 26, wherein the perfluorocarbon emulsion is administered to the subject at a rate of 15 ml/min.

28. The method of claim 1, wherein the perfluorocarbon is administered to the subject at a rate of 6.0-12.0 g/min.

29. The method of claim 28, wherein the perfluorocarbon is administered to the subject at a rate of 9.0 g/min.

30. The method of claim 1, wherein 0.3-2.1 g of perfluorocarbon per kilogram of subject's body weight is administered to the subject.

31. The method of claim 30, wherein 0.6-1.8 g of perfluorocarbon per kilogram of subject's body weight is administered to the subject.

32. The method of claim 1, wherein the administration of the perfluorocarbon does not increase free radical generation in a neuronal tissue of the subject.

33. The method of claim 1, further comprising administering to the subject an anti-coagulant and/or anti-inflammatory.

* * * * *